(12) United States Patent
Faldt et al.

(10) Patent No.: US 11,291,942 B2
(45) Date of Patent: Apr. 5, 2022

(54) BIOREACTOR CONDENSER

(71) Applicant: Cytiva Sweden AB, Uppsala (SE)

(72) Inventors: Eric Faldt, Uppsala (SE); Thomas Falkman, Uppsala (SE); Patric Fricking, Uppsala (SE); Patrick Jonsson, Uppsala (SE); Tomas Agren, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 1083 days.

(21) Appl. No.: 15/753,349

(22) PCT Filed: Aug. 23, 2016

(86) PCT No.: PCT/EP2016/069855
§ 371 (c)(1),
(2) Date: Feb. 19, 2018

(87) PCT Pub. No.: WO2017/036847
PCT Pub. Date: Mar. 9, 2017

(65) Prior Publication Data
US 2018/0243679 A1    Aug. 30, 2018

(30) Foreign Application Priority Data

Aug. 28, 2015    (GB) .................................... 1515330

(51) Int. Cl.
*B01D 5/00* (2006.01)
*F25B 9/04* (2006.01)
*B01D 46/42* (2006.01)
*B01D 53/00* (2006.01)
*B01D 53/26* (2006.01)
(Continued)

(52) U.S. Cl.
CPC ....... *B01D 46/4263* (2013.01); *B01D 5/0021* (2013.01); *B01D 5/0069* (2013.01);
(Continued)

(58) Field of Classification Search
CPC .. B01D 5/0021; B01D 5/0069; B01D 5/0072; B01D 5/0075; B01D 46/4263;
(Continued)

(56) References Cited

U.S. PATENT DOCUMENTS 3,942,330 A * 3/1976 Schroder ................ B01D 53/26
62/5
3,956,903 A    5/1976 Hiller et al.
(Continued)

FOREIGN PATENT DOCUMENTS

DE    3720259 A1    12/1988
DE    19625153 A1    1/1998
(Continued)

OTHER PUBLICATIONS

PCT International Search Report and Written Opinion for PCT Application No. PCT/EP2016/069855 dated Oct. 14, 2016 (10 pages).
(Continued)

*Primary Examiner* — Jonathan Miller
*Assistant Examiner* — Gabriel E Gitman
(74) *Attorney, Agent, or Firm* — Eversheds Sutherland (US) LLP

(57) ABSTRACT

The invention discloses a condenser for a bioreactor exhaust, comprising: an inlet (1) adapted to be fluidically connected to a bioreactor exhaust port (2), a cooling chamber (3; 103) fluidically connected to the inlet and via a filter device (4) to an outlet (5), a cooling conduit (6; 106) in contact with the cooling chamber, a heating conduit (7) in contact with the filter device and a vortex tube (8) arranged to convey a cold gas stream through the cooling conduit and to convey a hot gas stream through the heating conduit.

30 Claims, 5 Drawing Sheets

(51) Int. Cl.
  *F25B 39/04* (2006.01)
  *F25B 39/00* (2006.01)
  *C12M 1/00* (2006.01)
  *C12M 3/00* (2006.01)
  *C12M 1/02* (2006.01)

(52) U.S. Cl.
  CPC ......... *B01D 5/0072* (2013.01); *B01D 5/0075* (2013.01); *B01D 53/002* (2013.01); *B01D 53/265* (2013.01); *C12M 23/14* (2013.01); *C12M 23/26* (2013.01); *C12M 23/48* (2013.01); *C12M 27/00* (2013.01); *C12M 29/06* (2013.01); *C12M 29/20* (2013.01); *F25B 9/04* (2013.01); *F25B 39/00* (2013.01); *F25B 39/04* (2013.01)

(58) Field of Classification Search
  CPC .... B01D 53/002; B01D 53/265; C12M 23/14; C12M 23/26; C12M 23/48; C12M 27/00; C12M 29/06; C12M 29/20; F25B 9/04; F25B 39/00; F25B 39/04
  See application file for complete search history.

(56) References Cited

U.S. PATENT DOCUMENTS

| | | | |
|---|---|---|---|
| 5,483,801 A | * | 1/1996 | Craze ................... B01D 5/0084 62/5 |
| 8,455,242 B2 | | 6/2013 | Staheli et al. |
| 2012/0260671 A1 | | 10/2012 | Damren et al. |

FOREIGN PATENT DOCUMENTS

| | | | | |
|---|---|---|---|---|
| GB | 2028149 A | * | 3/1980 | ........... B01D 5/0006 |
| GB | 2028149 A | | 3/1980 | |
| JP | 2000-233168 A | | 8/2000 | |
| WO | 2011/114084 A1 | | 9/2011 | |

OTHER PUBLICATIONS

GB Search Report for GB Application No. 1515330.7 dated Jan. 18, 2016 (3 pages).

Japanese Office Action for JP Application No. 2018-511092 dated Apr. 13, 2020 (11 pages with English translation).

* cited by examiner

BIOREACTOR CONDENSER

CROSS REFERENCE TO RELATED APPLICATIONS

This application claims the priority benefit of PCT/EP2016/06855 filed on Aug. 23, 2016 which claims priority benefit of Great Britain Application No. 1515330.7 filed Aug. 28, 2015. The entire contents of which are hereby incorporated by reference herein.

TECHNICAL FIELD OF THE INVENTION

The present invention relates to bioreactors, and more particularly to a condenser for a bioreactor. The invention also relates to a method of cultivating cells in a bioreactor.

BACKGROUND OF THE INVENTION

Cell culturing is an essential step in manufacturing biological products, and may be carried out in disposable bioreactors systems or in non-disposable bioreactors such as steel tank vessels. Oxygen is continuously supplied to promote cell growth, and carbon dioxide is removed. A gas stream going to or coming from a bioreactor may contain moisture entrained within the gas stream. The moisture in the gas may condense as the gas passes through a filter or other system component. The moisture and/or condensation may be detrimental to the functioning of the filter or other system component. Further, loss of moisture with the gas stream may lead to undesired concentration increases in the cell culture.

Currently available condensers require the addition of a separate filter heater to avoid condensation of residual moisture in the filter. This increases complexity and accordingly there is a need for an integrated device providing both condensation and filter heating.

SUMMARY OF THE INVENTION

One aspect of the invention is to provide a condenser for a bioreactor exhaust with built-in filter heating. This is achieved with a condenser comprising an inlet adapted to be fluidically connected to a bioreactor exhaust port, a cooling chamber fluidically connected to the inlet and via a filter device to an outlet, at least one cooling conduit in contact with the cooling chamber, a heating conduit in contact with the filter device and a vortex tube arranged to convey a cold gas stream through the cooling conduit and to convey a hot gas stream through the heating conduit.

A technical advantage is that both cooling and heating is provided by a simple low-cost device which provides gas streams of suitable temperatures that can easily be conveyed to both a cooling chamber and a filter device.

A second aspect of the invention is to provide a bioreactor with a condenser. This is achieved with a bioreactor having a condenser as described above.

A third aspect of the invention is to provide a method for cell cultivation. This is achieved with a method comprising the steps of: providing a bioreactor as described above; adding culture medium and cells to the bioreactor; cultivating cells under agitation and addition of at least one gas to the bioreactor, wherein exhaust gas from the bioreactor is conveyed through the condenser to recycle a condensate to the bioreactor.

Further suitable embodiments of the invention are described in the dependent claims.

DRAWINGS

DEFINITIONS

Figure 1:
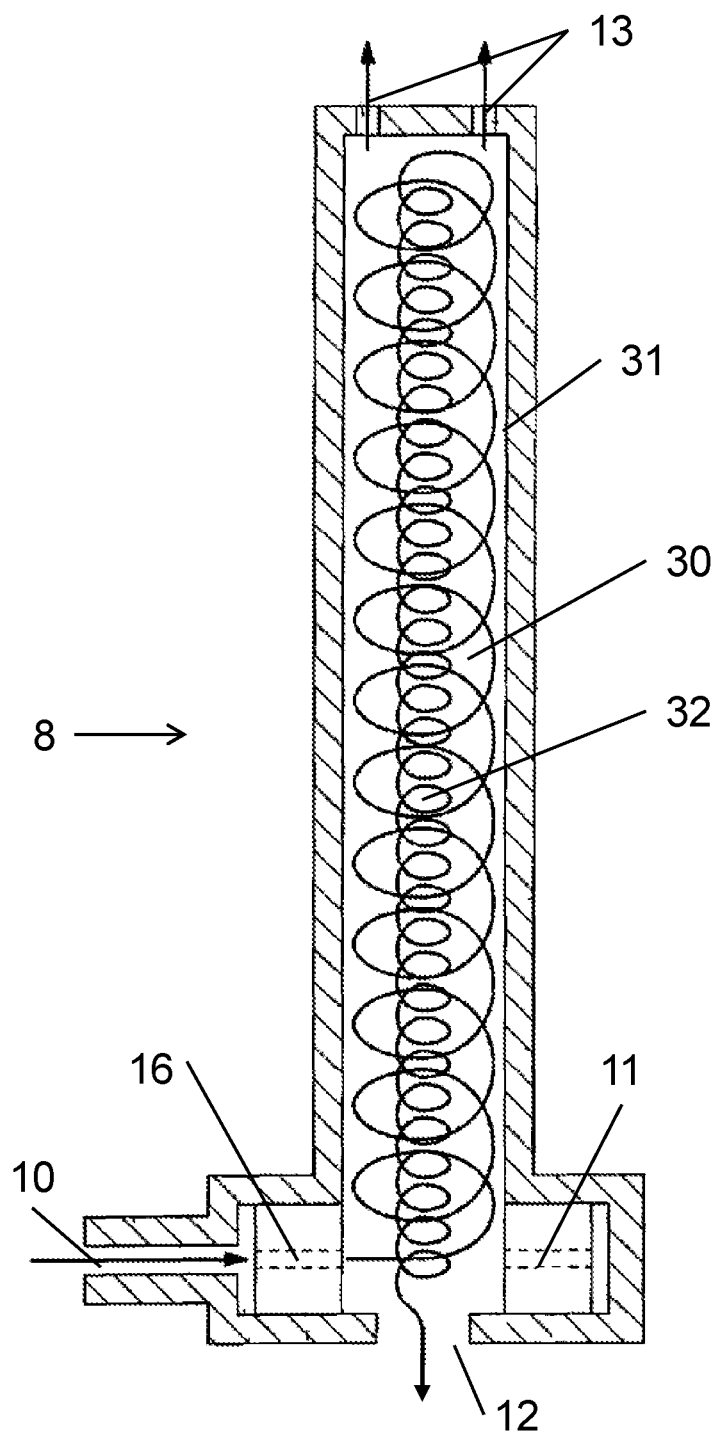
FIG. 1 shows a vortex tube for use with the invention.

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

Any directional terms such as "top", "bottom", "above", "below" "up", "down" and "height" herein refer to the devices as they appear in the drawings. Joinder references (e.g., joined, attached, coupled, connected, and the like) are to be construed broadly and may include intermediate members between a connection of elements and relative movement between elements. As such, joinder references do not necessarily imply that two elements are connected directly and in fixed relation to each other. Further, various elements discussed with reference to the various embodiments may be interchanged to create entirely new embodiments coming within the scope of the present invention.

The term "vortex tube" herein means a Ranque-Hilsch vortex tube (also called a Ranque tube, a Hilsch device or a Hilsch tube), well known in the art. General descriptions of vortex tubes are available in e.g. U.S. Pat. Nos. 1,952,281, 3,208,229, 3,461,676, 4,339,926 and 5,327,728, which are hereby incorporated by reference in their entireties.

DETAILED DESCRIPTION OF EMBODIMENTS

Figure 2:
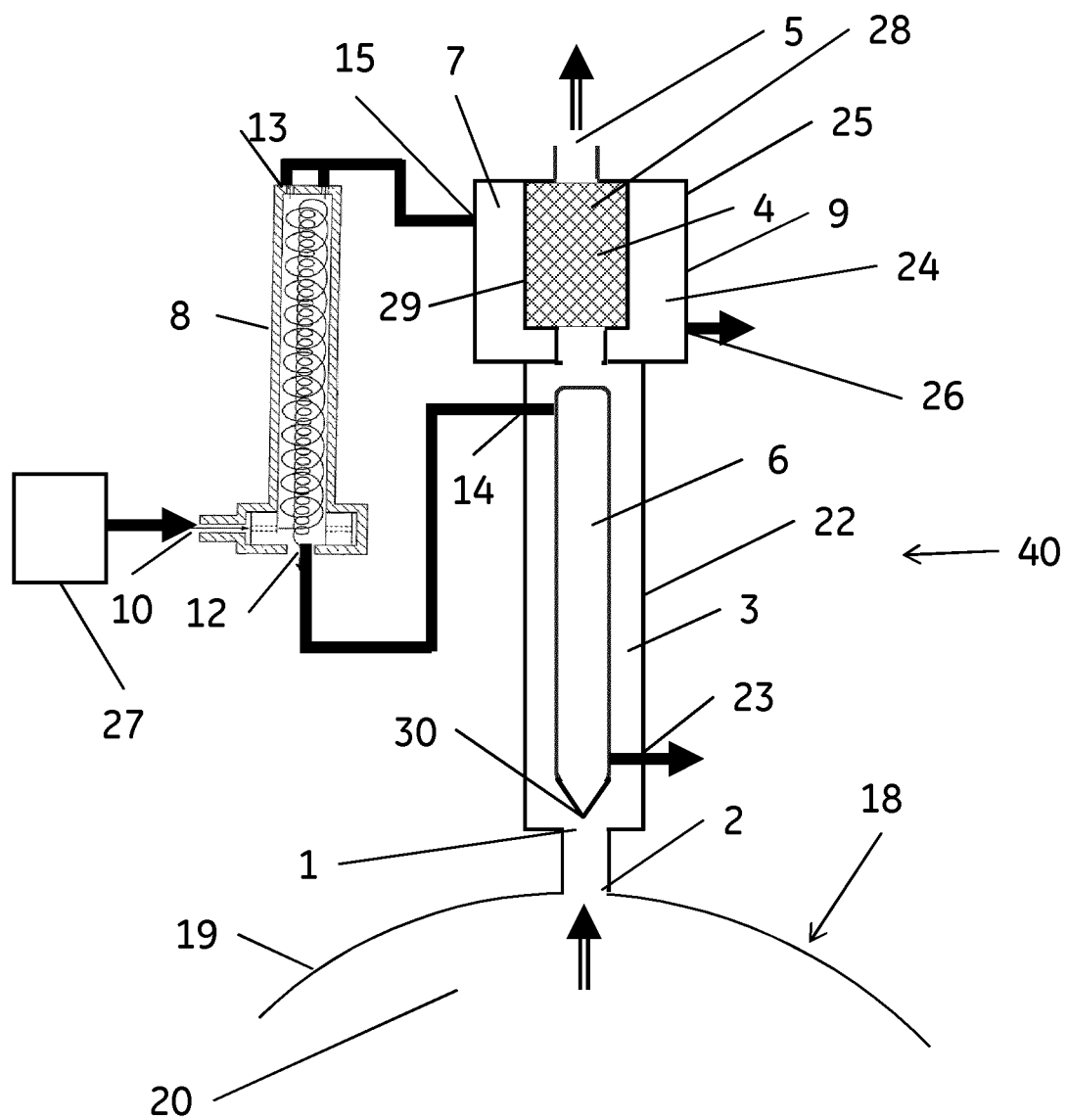
FIG. 2 shows a condenser of the invention and a bioreactor of the invention.
Figure 3:
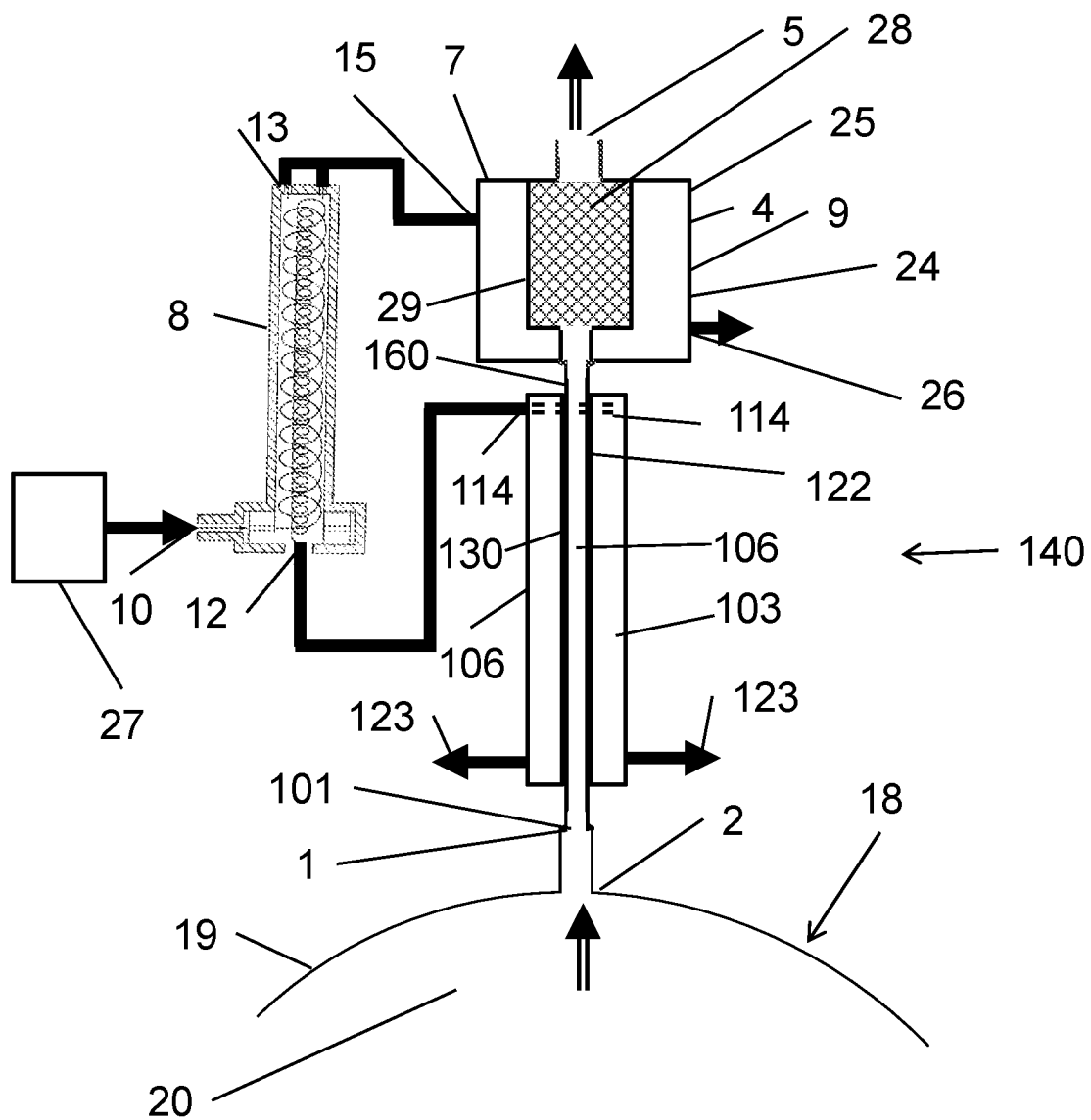
FIG. 3 shows a condenser of the invention and a bioreactor of the invention (side view).
Figure 4:
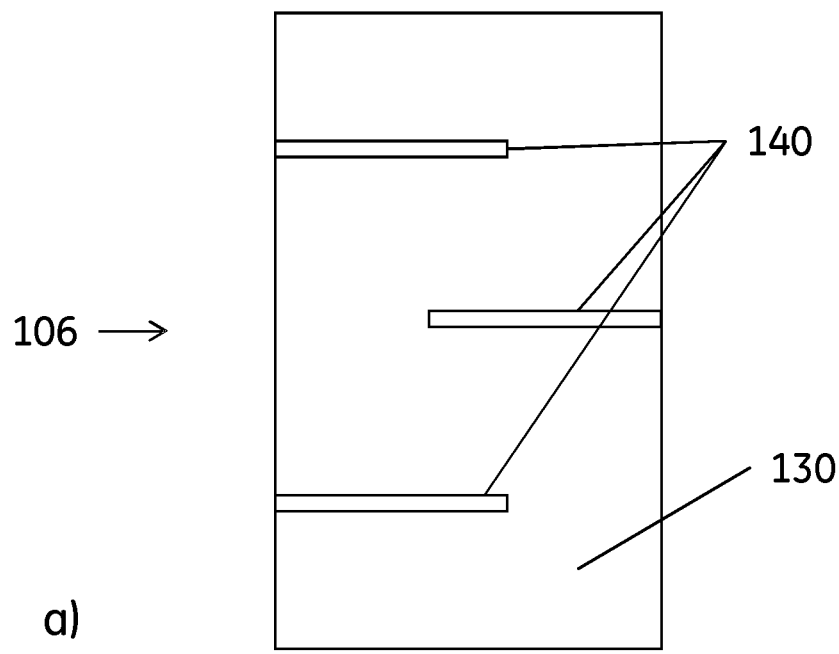
FIG. 4 shows a) a cooling conduit for the condenser of FIG. 3 (transverse view) and b) a cooling chamber for the condenser of FIG. 3 (transverse view).
Figure 4:
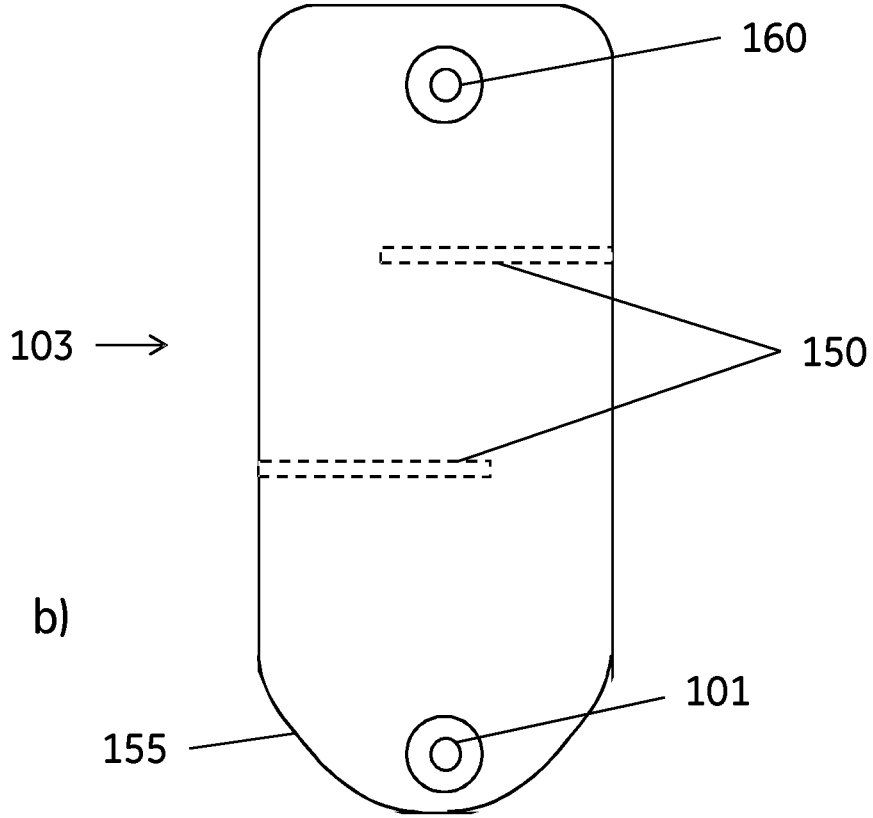

In one aspect, illustrated by FIGS. 1-3, the present invention discloses a condenser 40;140 for a bioreactor exhaust, which can alternatively be called a condenser apparatus. The condenser/condenser apparatus 40;140 comprises:

i) an inlet 1 which is adapted to be fluidically connected to a bioreactor exhaust port 2.

ii) a cooling chamber 3;103 fluidically connected, e.g. via a cooling chamber inlet 101 and a cooling chamber outlet 160, to the inlet 1 and via a filter device 4 to an outlet 5.

iii) at least one cooling conduit 6;106 in contact with the cooling chamber 3;103. The cooling conduit can e.g. be located inside the cooling chamber or it can form part of a wall 22 of the cooling chamber, be in direct contact with a wall 122 of the cooling chamber and/or have a wall 130 which is in direct contact with a wall 122 of the cooling chamber 103. The cooling conduit(s) can suitably have a cooling conduit inlet 14;114 and a cooling conduit outlet 23;123. In the case when the cooling conduit is located inside the cooling chamber, the cooling conduit inlet and cooling conduit outlet can suitably be located on the outside of the cooling chamber. The cooling conduit can e.g. be a straight tubular structure, a spiraling tubular structure or a plurality of tubular structures, e.g. a bundle of (suitably non-porous) hollow fibers. The cooling chamber may also be double-walled and the cooling conduit may comprise the interstitial volume between the double walls. Alternatively, as illustrated in FIG. 4 a), the cooling conduit(s) 106 can have a hollow generally rectangular box-like structure with a wall (also called a contacting surface) 130 arranged to contact a wall 122 of the cooling chamber 103. The cooling chamber 103 can, as illustrated in FIG. 4 b), e.g. be a flexible bag (e.g. a two-dimensional bag with a front wall and a back wall made from plastic film or laminate and welded together), which may have the cooling chamber inlet 101 and outlet 160 in the form of welded fittings, and it can be clamped or sandwiched between two box-like cooling conduits. As indicated in FIG. 4 b), a lower section of the cooling chamber bag may have a tapered or funnel-like shape, to facilitate condensate removal via inlet 101 which may be located at or adjacent the bottom of the bag, suitably at the narrow end of the tapered/funnel-like section. If bag 103 is a 3-dimensional bag, the lower section of the bag may be supported by one or more inclined support surfaces to provide a similar tapered/funnel-like shape. The cooling conduits may e.g. be connected by a hinge to facilitate the clamping and they may be locked in a clamping position e.g. by a latch. One or both of the cooling conduits may have one or more ribs 140 on the contacting surface 130 to locally compress a bag cooling chamber, creating a tortuous flowpath through the bag. The contacting surface 130 may be essentially flat, apart from the protruding ribs 140. Alternatively, or additionally, the bag cooling chamber 103 may have welded flow diverters 150 for creating the tortuous flowpath. The cooling conduit may advantageously have a wall thickness of less than 1.0 mm, such as 50 to 1000 or 50 to 500 micrometers to improve the heat transfer rate, particularly if the cooling conduit is made of plastics. Alternatively, or additionally, a wall 130 of the cooling conduit, arranged to contact a wall of the cooling chamber, can be made from a heat conductive material, such as a metal. It can e.g. be made of aluminium.

If the cooling conduit 6 is located inside the cooling chamber it may have a dripping nose 30 at a lower end to collect condensate, which can be returned to the bioreactor either through the inlet 1 or via a separate condensate line, e.g. by gravity.

iv) a heating conduit 7 in contact with the filter device 4. The filter device can e.g. be an encapsulated 29 filter medium 28 and it can further e.g. be mounted in an outer filter housing 9 and the heating conduit can optionally be located inside the outer filter housing, e.g. as an interstitial space 24 between the filter device and one or more walls 25 of the outer filter housing. The filter medium can e.g. be a membrane, such as a sterilization grade membrane, or a fibrous filter medium and it can e.g. be in a flat or pleated configuration. The heating conduit can suitably have a heating conduit inlet 15 and a heating conduit outlet 26. The condenser may be fitted with more than one filter device, which may be in contact with the same heating conduit or with different heating conduits. If one filter device is clogged, the flow can then be diverted to a new filter device using e.g. a valve or tubing clamps. If separate heating conduits are used, the hot air flow from the vortex tube may also be diverted to the heating conduit in contact with the new filter device.

v) a vortex tube 8, which is arranged to convey a cold gas stream through the cooling conduit 6 and to convey a hot gas stream through the heating conduit 7. The vortex tube 8 can suitably be generally cylindrical with at least one gas inlet 10 fluidically connected to a swirl generator 11, at least one cold gas outlet 12 and at least one hot gas outlet 13. The swirl generator (e.g. one or more nozzles or conduits 16 arranged tangentially to a periphery 31 of the inner volume 30 of the vortex tube) may be adapted to induce a rotating gas flow in the inner volume 30 of the vortex tube, causing an enrichment of hot gas near the periphery 31 of the inner volume and of cold gas near the center 32 of the volume. Accordingly, the hot gas outlet can be arranged to collect gas from the periphery and the cold gas outlet to collect gas from the center. The hot and cold gas outlets may be located at opposite ends of the tube, as in FIG. 1, or they may be located at the same end. The vortex tube may be adapted to receive a gas flow from a source of compressed gas (air) 27 through the gas inlet(s) and to supply a flow of gas having a temperature >25° C., such as >30° C. or 30-50° C. through the hot gas outlet and a flow of gas having a temperature <20° C., such as <10° C. or 0-10° C. through the cold gas outlet. Alternatively, or additionally, the vortex tube may be adapted to receive a gas (air) flow of temperature t from the gas source through the gas inlet(s) and to supply a flow of gas having a temperature >t+5° C., such as >t+10° C. or t+10° C. to t+30° C. through the hot gas outlet and a flow of gas having a temperature <t−5° C., such as <t−10° C. or t−20° C. to t−10° C. through the cold gas outlet. t can typically be the ambient temperature, room temperature or a temperature in the interval of 18-27° C. The gas inlet(s) can suitably be fluidically connected to a source of pressurized gas, e.g. compressed air, while the cold gas outlet can be fluidically connected to a cooling conduit inlet 14 and the hot gas outlet to a heating conduit inlet 15. Suitable vortex tubes are available from e.g. Nex Flow™ Air Products Corp., Ontario Canada, Exair Corp., Ohio USA, ITW Vortec and Arizona Vortex Tube Manufacturing Co., Arizona USA.

The condenser may further comprise a condensate line and optionally a condensate pump (not shown) for conveying condensate back to a bioreactor 18. A separate condensate line and condensate pump are particularly suitable in the case of large bioreactors, where large amounts of condensate are produced.

In some embodiments, the cooling chamber with the cooling conduit and the filter device with the heating conduit and optionally the outer filter housing are disposable, to eliminate the need for cleaning/sanitation between different cultivations. At least one of the cooling chamber, the cooling conduit and the outer filter housing can be manufactured from plastics to enable use as disposables/single use components. The filter device may likewise consist or consist essentially of a filter medium 28 (e.g. a membrane or a fibrous filter medium) and plastic components, including the encapsulation 29. At least the cooling chamber, the cooling conduit, the filter device and the outer filter housing may further be preassembled and supplied as a packaged sterile/presterilized or microbially controlled unit, to facilitate disposable use. The sterilization or microbial control can be achieved e.g. by gamma irradiation. Microbial control means that the bioburden is decreased, e.g. by irradiation, but the sterility does not need to be validated.

In certain embodiments, the vortex tube is mounted on, or integral with, the cooling chamber or cooling conduit. Alternatively, the cooling chamber, the cooling conduit, the filter device, the heating conduit and the optional outer filter housing can be mounted on the vortex tube.

In a second aspect, the invention discloses a bioreactor with the condenser/condenser apparatus 40 as discussed above fluidically connected to an exhaust port 2 on the bioreactor. The bioreactor may e.g. comprise a collapsible bag 19, and the exhaust port may be fluidically connected to an interior volume 20 of the collapsible bag. Suitable bioreactors with collapsible bags for use with the condenser of the invention include e.g. those described in US2005/0272146 and U.S. Pat. No. 6,190,913, which are hereby incorporated by reference in their entireties. The collapsible bag can e.g. be supported and surrounded by a rigid support structure/support vessel, or it can be supported by a tray on a rocking platform. Further, the collapsible bag may comprise at least one sparger and/or at least one agitator. The bioreactor or the collapsible bag may have an interior volume of at least 1 L, such as at least 10 L, 1-2500 L or 10-1000 L.

In a third aspect, the invention discloses a method of cultivating cells in a bioreactor, comprising the steps of:

a) providing a bioreactor as described above;

b) adding culture medium and cells to the bioreactor. The cells can be e.g. animal cells (such as mammalian or insect cells) or microbial cells (such as bacteria or yeast cells) and the cell lines may optionally be selected to express a biopharmaceutical, e.g. a therapeutic protein or a vaccine antigen;

c) cultivating cells under agitation and addition of at least one gas to the bioreactor, wherein exhaust gas from the bioreactor is conveyed through the condenser to recycle a condensate to the bioreactor. The gas inlet(s) 10 is/are suitably fluidically connected to a source of pressurized gas, e.g. compressed air, while the cold gas outlet is suitably fluidically connected to a cooling conduit inlet 14 and the hot gas outlet to a heating conduit inlet 15. The gas delivered through the hot gas outlet 13 may e.g. have a temperature >25° C., such as >30° C. or 30-50° C. through the hot gas outlet and the gas delivered from the cold gas outlet 12 may e.g. have a temperature <20° C., such as <10° C. or 0-10° C.

EXAMPLE 1

A condenser corresponding to FIG. 2 was set up, with a vortex tube fed with 3.0 bar (300 kPa) pressurized air at 20° C. and the inlet 1 was connected to a glass bottle partly filled with 80° C. water, through which air was pumped via an immersed dip tube at a controlled rate (WM 400 peristaltic pump at 400 rpm). The residual moisture in the stream at the outlet 5 was measured by conducting the stream through a glass bottle immersed in ice water and weighing the bottle. The experiment was conducted for 3.5 h.

Results

The hot air supplied from the vortex tube to the filter heater had a temperature of 34° C. and the cold air supplied to the cooling conduit had a temperature of 5.3° C. When the vortex tube was running, 1 g/h residual moisture was found in the cooling conduit outlet stream, compared to 16 g/h when no pressurized air was supplied to the vortex tube.

Since vortex tubes are known to produce a hissing noise, the noise level of the condenser was measured, but was found to be max. 55 dB (5.4 kHz), presumably due to the muffling effect of the cooling conduit and the outer filter housing. This level is acceptable in a bioprocess production setting.

EXAMPLE 2

A condenser corresponding to FIG. 3 was set up, with a vortex tube fed with 3.0 bar (300 kPa) pressurized air at 20° C. and the inlet 1 was connected by tubing to an XDR 10 single use bioreactor (GE Healthcare Life Sciences) having a 10 L flexible bag bioreactor supported by a stainless steel support vessel. The condenser had two 10×20 cm rectangular box-like cooling conduits, with aluminium plates as contacting surfaces and 3D printed back pieces comprising inlets and outlets for the cold air from the vortex tube. The cooling conduits were connected by hinges on one of the 20 cm sides and could be locked into a clamping position by a latch. The cooling chamber was a 10×39 cm two-dimensional bag made from two welded plastic laminate sheets. The bag had an inlet at the bottom and an outlet at the top, in the form of welded ports on one of the laminate sheets and parts of the bag extended outside the cooling conduit boxes. The bag outlet was connected by tubing to a sterile filter positioned inside a heating conduit connected to the hot air supply from the vortex tube. A microbial cultivation was conducted in the bioreactor and the condensate produced in the condenser was fed back to the bioreactor. The temperature at the bag inlet and outlet, as well as the temperature of a cooling conduit was monitored with a thermal camera.

Figure 5:
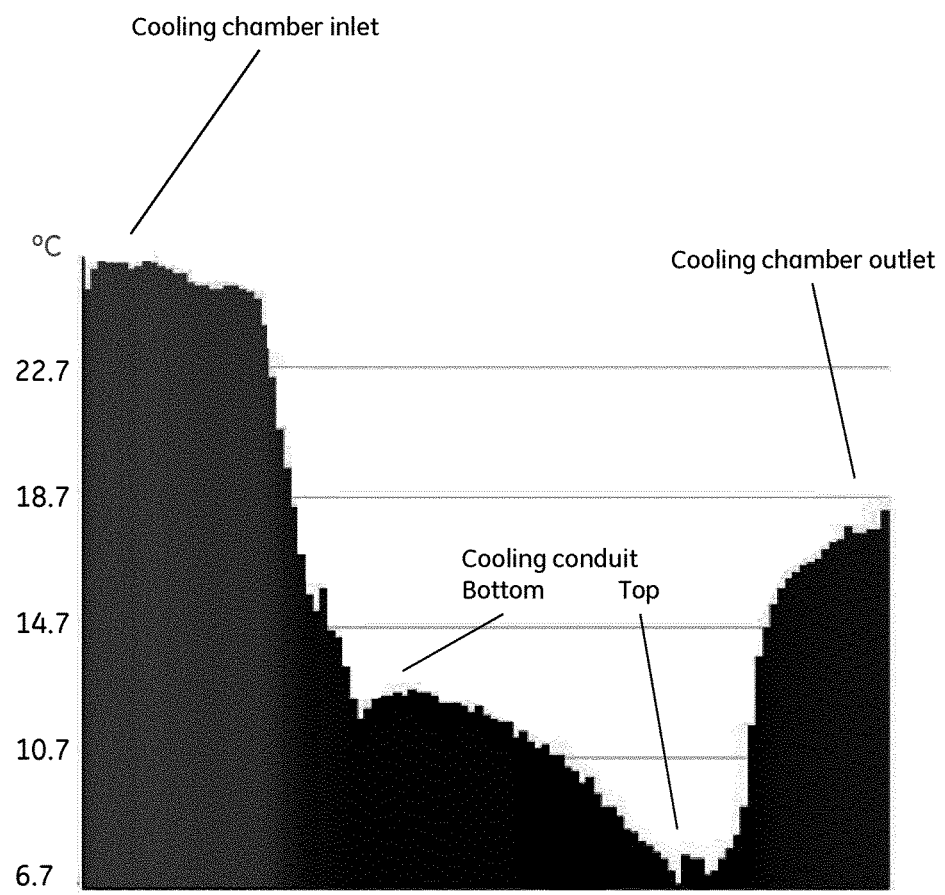
FIG. 5 shows the temperature profile over the bag cooling chamber and cooling conduit during the run of Example 2.

Results (FIG. 5)

The bag inlet connected to the bioreactor had a temperature of about 26° C. and the bag outlet had a temperature of about 17° C. The cooling conduit (fed from the top with cold air from the vortex tube) had a temperature of about 7° C. at the top and about 13° C. at the bottom. 65-70% of the liquid evaporated from the bioreactor was condensed and returned to the bioreactor. The lifetime of the exhaust filter before clogging was considerably prolonged by the use of the condenser.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Any patents or patent applications mentioned in the text are hereby incorporated by reference in their entireties, as if they were individually incorporated.

The invention claimed is:

1. A condenser for a bioreactor exhaust, comprising:
    an inlet adapted to be fluidically connected to a bioreactor exhaust port, a cooling chamber fluidically connected to said inlet and to an outlet via a filter device, at least one cooling conduit in contact with said cooling chamber, a heating conduit in contact with said filter device, and a vortex tube arranged to convey a cold gas stream through said at least one cooling conduit and to convey a hot gas stream through said heating conduit, wherein said filter device is mounted in an outer filter housing and said heating conduit is located inside the outer filter housing.

2. The condenser of claim 1, wherein said at least one cooling conduit is located inside said cooling chamber.

3. The condenser of claim 1, wherein said at least one cooling conduit forms part of a wall of said cooling chamber or is in direct contact with a wall of said cooling chamber.

4. The condenser of claim 1, wherein a wall of said at least one cooling conduit is in direct contact with a wall of said cooling chamber.

5. The condenser of claim 1, wherein said cooling chamber is a flexible bag.

6. The condenser of claim 4, wherein said at least one cooling conduit is two cooling conduits, and wherein said cooling chamber is clamped or sandwiched between said two cooling conduits.

7. The condenser of claim 1, wherein said vortex tube is generally cylindrical and comprises at least one gas inlet connected to a swirl generator, a cold gas outlet and a hot gas outlet.

8. The condenser of claim 7, wherein said vortex tube is adapted to receive a gas flow through said at least one gas inlet and to supply said hot gas stream through said hot gas outlet, wherein said hot gas steam has a temperature >25° C., and wherein said vortex tube is adapted to supply said cold gas stream through said cold gas outlet, wherein said cold gas stream has a temperature <20° C.

9. The condenser of claim 7, wherein said vortex tube is adapted to receive a gas flow of temperature t through said at least one gas inlet and to supply said hot gas stream through said hot gas outlet, wherein said hot gas stream has a temperature >t+5° C., and wherein said vortex tube is adapted to supply said cold gas stream through said cold gas outlet, wherein said cold gas stream has a temperature <t−5° C.

10. The condenser of claim 9, wherein t is a temperature in the interval of 18-27° C.

11. The condenser of claim 7, wherein said at least one gas inlet is connected to a source of pressurized gas, said cold gas outlet is connected to a cooling conduit inlet and said hot gas outlet is connected to a filter heating inlet.

12. The condenser of claim 7, wherein at least the cooling chamber and the outer filter housing are manufactured from plastics.

13. The condenser of claim 7, wherein at least the cooling chamber, the filter device and the outer filter housing are preassembled and supplied as a packaged presterilized or microbially controlled unit.

14. The condenser of claim 7, wherein the vortex tube is mounted on, or integral with, said cooling chamber and/or said at least one cooling conduit.

15. The condenser of claim 1, wherein the cooling chamber, the at least one cooling conduit, the filter device and the outer filter housing are mounted on the vortex tube.

16. The condenser of claim 1, wherein said at least one cooling conduit has a wall thickness of less than 1.0 mm.

17. The condenser of claim 1, wherein a wall of said at least one cooling conduit, arranged to contact a wall of said cooling chamber, is made from a heat conductive material.

18. The condenser of claim 1, further comprising a condensate line and optionally a condensate pump for conveying condensate back to a bioreactor.

19. The condenser of claim 1, wherein said at least one cooling conduit has a wall thickness of 50 to 500 micrometers.

20. The condenser of claim 17, wherein the heat conductive material is metal.

21. A bioreactor with the condenser of claim 1 fluidically connected to the bioreactor exhaust port.

22. The bioreactor of claim 21, comprising a collapsible bag, wherein said bioreactor exhaust port is fluidically connected to an interior volume of said collapsible bag.

23. The bioreactor of claim 22, wherein said collapsible bag is supported and surrounded by a rigid support structure.

24. The bioreactor of claim 21, having an interior volume of at least 1 L.

25. The bioreactor of claim 22, further comprising at least one sparger and/or at least one agitator.

26. The bioreactor of claim 21, having an interior volume of 10-1000 L.

27. A method of cultivating cells in a bioreactor, comprising the steps of:
   a) providing a bioreactor according to claim 21;
   b) adding culture medium and cells to said bioreactor;
   c) cultivating cells under agitation and addition of at least one gas to said bioreactor, wherein exhaust gas from said bioreactor is conveyed through said condenser to recycle a condensate to said bioreactor.

28. The method of claim 27, wherein said cells are animal cells or microbial cells.

29. The method of claim 27, wherein said cells express a biopharmaceutical.

30. The method of claim 29, wherein the biopharmaceutical is a therapeutic protein or a vaccine antigen.

* * * * *